United States Patent [19]

Kamon

[11] Patent Number: 5,291,773
[45] Date of Patent: Mar. 8, 1994

[54] APPARATUS AND METHOD FOR ULTRASONIC DETECTION OF FOREIGN MATERIALS IN A SPECIMEN

[75] Inventor: Kazuya Kamon, Itami, Japan

[73] Assignee: Mitsubishi Denki Kabushiki Kaisha, Tokyo, Japan

[21] Appl. No.: 780,224

[22] Filed: Oct. 22, 1991

[30] Foreign Application Priority Data

Dec. 28, 1990 [JP] Japan .................................. 2-417788

[51] Int. Cl.⁵ ............................................. G01N 29/02
[52] U.S. Cl. ................................ 73/24.03; 73/61.75;
73/64.53; 73/606; 73/865.5
[58] Field of Search ................. 73/24.03, 61.75, 64.53,
73/61.49, 606, 865.5, 642

[56] References Cited

U.S. PATENT DOCUMENTS

| | | | |
|---|---|---|---|
| 2,966,056 | 12/1960 | Heller | 73/61.75 |
| 3,911,726 | 10/1975 | Georgieu | 73/64.53 |
| 4,193,473 | 3/1980 | Hartemann | 73/642 |
| 4,457,757 | 7/1984 | Ramsey, Jr. et al. | 73/606 |
| 4,527,420 | 7/1985 | Foote | 73/61.75 |
| 4,542,644 | 9/1985 | Claytor et al. | 73/61.75 |
| 4,580,444 | 4/1986 | Abts et al. | 73/61.75 |
| 4,718,269 | 1/1988 | Der Kinderen | 73/24.03 |

*Primary Examiner*—Hezron E. Williams
*Assistant Examiner*—Rose M. Finley
*Attorney, Agent, or Firm*—Leydig, Voit & Mayer

[57] ABSTRACT

Foreign materials in a chemical specimen are detected by irradiating the chemical specimen with ultrasonic waves and detecting and monitoring scattered sound from the foreign materials in the chemical specimen. Even if the foreign materials are photosensitive substances which cannot be exposed to light, they can be detected.

5 Claims, 2 Drawing Sheets

APPARATUS AND METHOD FOR ULTRASONIC DETECTION OF FOREIGN MATERIALS IN A SPECIMEN

BACKGROUND OF THE INVENTION

1. Field of the Invention

The present invention relates to an apparatus and process for detecting foreign materials and, more particularly, to an apparatus and process for detecting foreign materials for use in LSI manufacturing processes.

2. Description of the Related Art

FIG. 2 shows a schematic perspective view illustrating a conventional apparatus for detecting foreign materials. In this figure, a chemical specimen 1 flows through a container in the form of a transparent pipe 2. An observation region 3 for the chemical specimen 1, as illustrated partially cutaway, is irradiated with a laser beam 4 such as an He-Ne laser beam through a projection optical system 5. The scattered light of this laser beam 4 is formed into an image at an image-formation region 7 through a receptor lens system 6.

In a conventional apparatus for detecting foreign materials of this type, the chemical specimen 1 enters the observation region 3 through the transparent pipe 2 and circulates through a return passage which is not illustrated. The observation region 3 is irradiated with the laser beam 4 through the projection optical system 5 and the laser beam 4 passes through the chemical specimen 1.

When foreign materials exist in the chemical specimen 1, the laser beam 4 is diffused to form scattered light. This scattered light is projected on image-formation region 7 through a receptor lens system 6. The foreign materials have been detected by monitoring the scattered light.

In the above apparatus for detecting foreign materials, since a laser beam is used, a transparent pipe 2 must be employed. Accordingly, it is difficult to employ this apparatus when the chemical specimen 1 is a photosensitive substance such as a photoresist.

SUMMARY OF THE INVENTION

Accordingly, an object of the invention is to solve such problems. More specifically, the object of the present invention is to provide an apparatus and process for detecting foreign materials which can be employed even for photosensitive chemicals having photosensitivity.

In order to achieve the above object, according to one aspect of the present invention, there is provided an apparatus for detecting foreign materials comprising: an ultrasonic wave generating means; a directional sound system for directing ultrasonic waves generated at the ultrasonic waves generating means to a specimen; a projection sound system for projecting scattered sound from the specimen on an image-formation region; and sound receiving means for receiving scattered sound from the image-formation region.

According to another aspect of the present invention, there is provided a process for detecting foreign materials contained in a chemical specimen comprising the steps of: generating ultrasonic waves; directing the ultrasonic waves at a specimen and irradiating the specimen therewith; projecting scattered sound from the specimen to an image-formation region; and receiving the scattered sound from the image-formation region.

DESCRIPTION OF THE PREFERRED EMBODIMENTS

Figure 1:
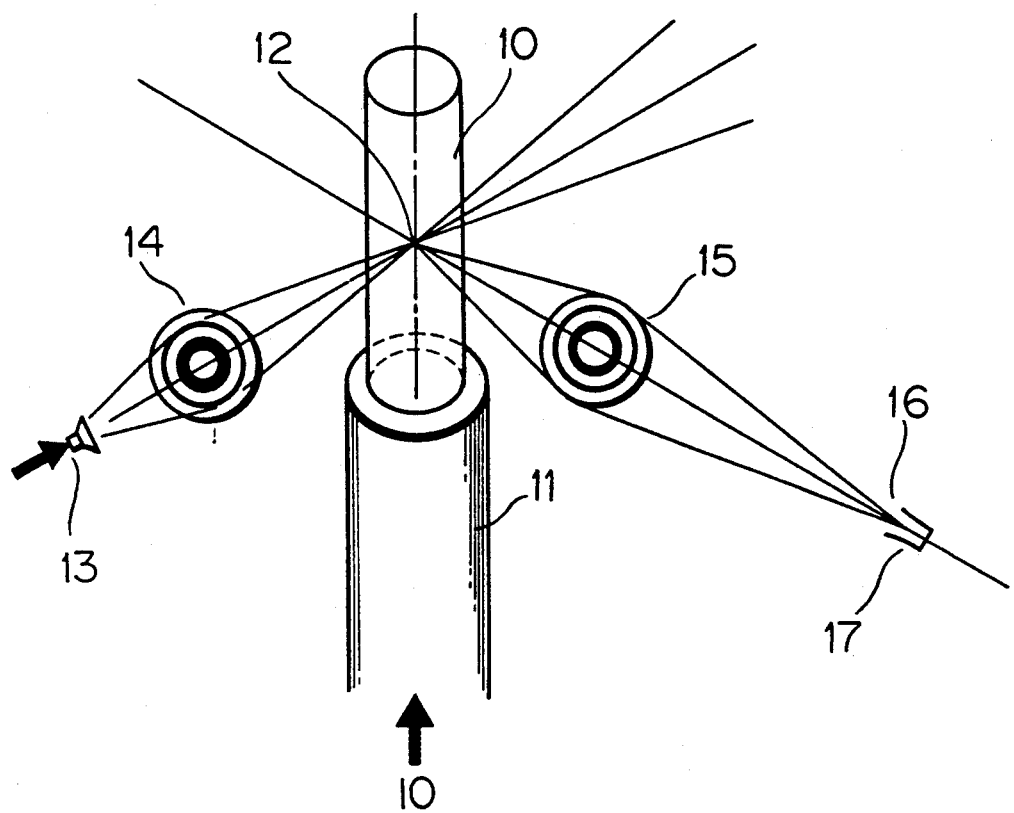
FIG. 1 is a schematic perspective view illustrating an embodiment of an apparatus for detecting foreign materials in accordance with the present invention.
Figure 2:
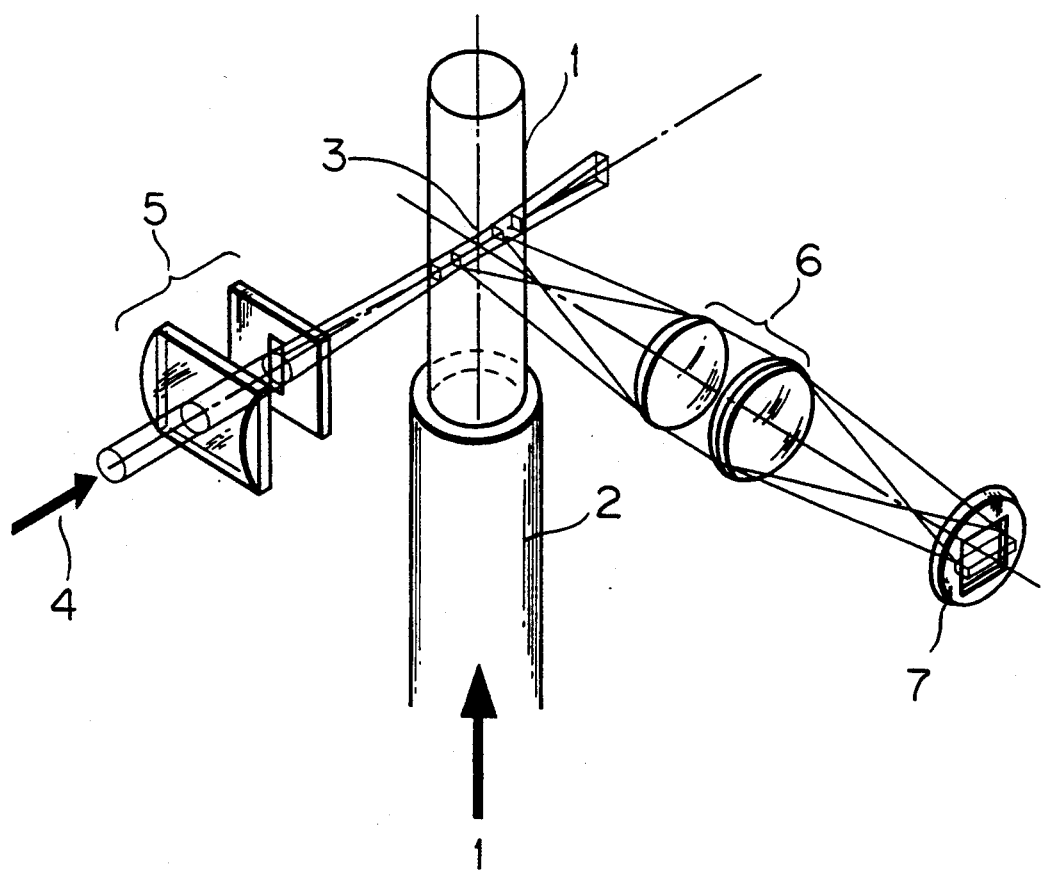
FIG. 2 is a schematic perspective view illustrating a conventional apparatus for detecting foreign materials.

FIG. 1 is a schematic perspective illustration of an embodiment of an apparatus for detecting foreign materials in accordance with the present invention. Chemical specimen 10 enters an observation region 12 in a container in the form of a pipe 11 and circulates through a return pipe which is not illustrated. The observation region 12 is irradiated with ultrasonic waves produced by an ultrasonic wave generator 13 spaced from the pipe 11 and condensed through the wall of the pipe 11 by a directional sound system such as a Fresnel lens 14. The irradiated ultrasonic waves are scattered by foreign materials in the chemical specimen 10. This scattered sound passes through the wall of the pipe 11 and is received by the use of a sound receiving means such as a microphone 17 in an image-formation region 16 through a Fresnel lens 15 in a projection sound system.

In the apparatus for inspecting foreign materials thus constructed, the chemical specimen 10 can contain substances which cannot be exposed to light, such as photosensitive substances. The pipe 11 can be made of metal, glass, and the like. When the chemical specimen 10 is photosensitive, a suitable opaque pipe can be used.

Ultrasonic waves produced by the ultrasonic wave generator 13 can be directed and condensed by the Fresnel lens 14. The ultrasonic waves reach an observation region 16 and pass through the chemical specimen 10. In this instance, if the chemical specimen contains foreign materials, the ultrasonic waves are diffused and produce scattered sound. This scattered sound is formed into an image in the image-formation region through the fresnel lens 15 in a sound receiving system and is subsequently received by a microphone 17. The foreign materials contained in the chemical specimen 10 are detected by monitoring this scattered sound. When the chemical specimen 10 is a substance which cannot be exposed to light, such as a photosensitive substance, this apparatus for detecting foreign materials is particularly effective. The foreign materials can also be quantitatively detected by previously passing a control specimen through the pipe 11 in order to determine the level of the scattered sound, followed by obtaining the scattered sound of the chemical specimen.

In the above preferred embodiment, the directional sound system and projection sound system employ a round Fresnel lens, but a linear Fresnel zone plate can also be used.

What is claimed is:

1. An apparatus for detecting foreign materials comprising:
    a container having a wall surrounding an observation region;
    an ultrasonic wave generator dispensed outside and spaced from the container for generating ultrasonic waves;
    sound directing means disposed between and spaced from the container and the wave generator for directing and condensing in the observation region the ultrasonic waves generated by the ultrasonic wave generator;

a sound detector disposed outside of and spaced from the container for detecting ultrasonic waves; and sound projecting means disposed between and spaced from the container and the sound detector for projecting ultrasonic waves scattered from the observation region to the sound detector.

2. The apparatus as defined in claim 1 wherein at least one of the sound directing means and the sound projecting means comprises a Fresnel lens.

3. The apparatus as defined in claim 1 wherein at least one of the sound directing means and the sound projecting means comprises a linear Fresnel zone plate.

4. The apparatus as defined in claim 1 wherein the container comprises a pipe for transporting a chemical specimen.

5. The apparatus as claimed in claim 4 wherein the pipe is opaque.

* * * * *

UNITED STATES PATENT AND TRADEMARK OFFICE
CERTIFICATE OF CORRECTION

PATENT NO. : 5,291,773
DATED : March 8, 1994
INVENTOR(S) : Kazuya Kamon

It is certified that error appears in the above-indentified patent and that said Letters Patent is hereby corrected as shown below:

On the title page:
Item [56], References Cited, under U.S. Patent Documents, change "4,457,757 7/1984 Ramsey, Jr. et al. 73/642" to --4,457,175 7/1984 Ramsey, Jr. et al. 73/642--.

Col. 2, line 63, change "dispensed" to --disposed--.

Signed and Sealed this

Twenty-sixth Day of July, 1994

Attest:

BRUCE LEHMAN

*Attesting Officer*  *Commissioner of Patents and Trademarks*